United States Patent [19]

Franke

[11] 4,007,175
[45] Feb. 8, 1977

[54] 2,4,6-SUBSTITUTED-3,5-DIOXO-1,2,4,6-THIATRIAZINES

[75] Inventor: Hans Georg Franke, Orinda, Calif.

[73] Assignee: Chevron Research Company, San Francisco, Calif.

[22] Filed: Aug. 4, 1975

[21] Appl. No.: 601,871

Related U.S. Application Data

[60] Continuation-in-part of Ser. No. 453,149, March 21, 1974, Pat. No. 3,915,688, which is a division of Ser. No. 146,498, May 24, 1971, Pat. No. 3,817,993.

[52] U.S. Cl. .................................. 260/243 R; 71/90
[51] Int. Cl.$^2$ ........................................ C07D 285/00
[58] Field of Search ................................ 260/243 R

[56] References Cited

UNITED STATES PATENTS 3,817,993  6/1974  Franke .............................. 260/243

Primary Examiner—John M. Ford
Attorney, Agent, or Firm—George F. Magdeburger; Dix A. Newell; Raymond Owyang

[57] ABSTRACT

Compounds of the formula

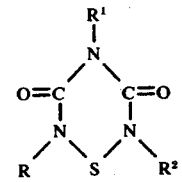

wherein R, $R^1$ and $R^2$ are independently hydrogen; alkoxy of 1 to 6 carbon atoms; aliphatic or cycloaliphatic hydrocarbyl of 1 to 10 carbon atoms optionally substituted wih halogen atoms; carbocyclic aryl of 6 to 15 carbon atoms optionally substituted with halogen atoms, nitro groups, alkyl groups, alkoxy groups or trifluoromethyl; or a heterocyclic group of 1 hetero oxygen, sulfur or nitrogen atoms and 4 to 5 annular carbon atoms and a total of 4 to 8 carbon atoms, find use as herbicides.

3 Claims, No Drawings

2,4,6-SUBSTITUTED-3,5-DIOXO-1,2,4,6-THIATRIAZINES

RELATED APPLICATIONS

This application is a continuation-in-part of application Ser. No. 453,149, filed Mar. 21, 1974, now U.S. Pat. No. 3,915,688, which in turn is a division of application Ser. No. 146,498, filed May 24, 1971, now U.S. Pat. No. 3,817,993, the disclosures of which applications are herein incorporated by reference.

BACKGROUND OF THE INVENTION

1. Field

The present invention is directed to 2,4,6-substituted-3,5-dioxo-1,2,4,6-thiatriazines, particularly 2-aryl-3,5-dioxo-4,6-substituted-1,2,4,6-thiatriazines and their use as herbicides.

2. Prior Art

U.S. Pat. No. 3,435,031 discloses certain 3,5-dioxotetrahydro-1,2,4,6-thiatriazine-1,1-dioxides and their use as bactericides, fungicides, etc.

DESCRIPTION OF THE INVENTION

The compounds of the present invention can be represented by the formuala

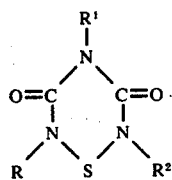

wherein R, $R^1$ and $R^2$ are individually hydrogen; alkoxy of 1 to 6 carbon atoms; aliphatic hydrocarbyl group of 1 to 10 carbon atoms substituted with 0 to 4 halogen atoms of atomic number 9 to 35 (fluorine, chlorine or bromine); cycloaliphatic hydrocarbyl group of 3 to 10 carbon atoms substituted with 0 to 4 halogen atoms of atomic number 9 to 35; carbocyclic aryl of 6 to 15 carbon atoms substituted with 0 to 5 halogen atoms of atomic number 9 to 35, nitro groups, alkyl groups of 1 to 4 carbon atoms, alkoxy groups of 1 to 4 carbon atoms or 0 to 1 trifluoromethyl; or a heterocyclic group of 1 hetero oxygen, sulfur or nitrogen and 4 to 5 annular carbon atoms and a total of 4 to 8 carbon atoms; with the proviso that at least one of R, $R^1$ or $R^2$ is alkoxy of 1 to 6 carbons.

Preferably $R^1$ is alkoxy of 1 to 6 carbon atoms and one of R and $R^2$ is aryl of 6 to 15 carbon atoms substituted with 0 to 5 halogen atoms of atomic number 9 to 35, nitro groups, alkyl groups of 1 to 4 carbon atoms or alkoxy groups of 1 to 4 carbon atoms or 0 to 1 trifluoromethyl and the other of R and $R^2$ is hydrogen, alkoxy of 1 to 6 carbon atoms, aliphatic hydrocarbyl groups of 1 to 10 carbon atoms substituted with 0 to 4 halogen atoms of atomic number 9 to 35 or cycloaliphatic hydrocarbyl group of 3 to 10 carbon atoms substituted with 0 to 4 halogen atoms of atomic number 9 to 35.

Still more preferably, R is hydrogen or aliphatic hydrocarbyl of 1 to 10 carbon atoms substituted with 0 to 4 halogen atoms of atomic number 9 to 35, $R^1$ is alkoxy of 1 to 6 carbon atoms and $R^2$ is aryl of 6 to 15 carbon atoms substituted with 0 to 5 halogen atoms of atomic number 9 to 35, nitro groups, alkyl groups of 1 to 4 carbon atoms or alkoxy groups of 1 to 4 carbon atoms or 0 to 1 trifluoromethyl.

The aliphatic hydrocarbyl groups which R, $R^1$ and $R^2$ may represent are alkyl of 1 to 10 carbon atoms, alkenyl of 2 to 10 carbon atoms or alkynyl of 2 to 10 carbon atoms, said alkyl, alkenyl or alkynyl being optionally substituted with up to 4 halogen atoms of atomic number 9 to 35. Preferably the aliphatic hydrocarbyl group will only contain up to 6 carbon atoms. Furthermore, it is preferred that the aliphatic hydrocarbyl group be alkyl or alkenyl or haloalkyl or haloalkenyl.

The cycloaliphatic hydrocarbyl group which R, $R^1$ and $R^2$ may represent include cycloalkyl and cycloalkenyl, said cycloalkyl or cycloalkenyl being optionally substituted with up to 4 halogen atoms of atomic number 9 to 35. Preferably the cycloaliphatic hydrocarbyl group will contain 3 to 6 carbon atoms, and more preferably will be cycloalkyl.

The aryl groups which R, $R^1$ and $R^2$ can represent are preferably of 6 to 15 carbon atoms substituted with 0 to 5 halogen atoms of atomic number 9 to 35, preferably fluorine or chlorine, 0 to 2 nitro groups or 0 to 3 alkyl groups of 1 to 4 carbon atoms or 0 to 3 alkoxy groups of 1 to 4 carbon atoms. Preferably the number of substituents on the aryl groups will not exceed 3 and preferably not exceed 2. The aryl group is preferably phenyl substituted with 0 to 5 halogen atoms of atomic number 9 to 35, nitro groups, alkyl groups of 1 to 4 carbon atoms or alkoxy groups of 1 to 4 carbon atoms. Even more preferably, the aryl is phenyl substituted with 0 to 2 halogen atoms of atomic number 9 to 35, preferably fluorine or chlorine, 0 to 1 alkyl group of 1 to 4 carbon atoms, preferably methyl, or 0 to 1 alkoxy group of 1 to 4 carbon atoms, preferably methoxy.

It is preferred that R be alkyl of 1 to 6 carbon atoms, preferably 1 to 4 carbon atoms, substituted with 0 to 3 halogen atoms of atomic number 9 to 35. Still more preferably, R will be unsubstituted alkyl of 1 to 4 carbon atoms, preferably 1 to 3 carbon atoms.

It is preferred that $R^1$ be alkoxy of 1 to 6 carbon atoms. More preferably $R^1$ is alkoxy of 1 to 3 carbon atoms.

Representative aliphatic hydrocarbyl groups which R, $R^1$ and $R^2$ can represent include methyl, ethyl, n-propyl, isopropyl, n-butyl, sec-butyl, isobutyl, t-butyl, pentyl, hexyl, octyl, nonyl, decyl, vinyl, allyl, crotyl, 4-pentenyl, 3-hexenyl, 4-decenyl, propargyl, chloromethyl, dichloromethyl, trichloromethyl, fluoromethyl, tetrachloroethyl, 1-chloroethyl, 1,2-dichloroethyl, 2,2-dibromopropyl, 1,2,6-trichlorohexyl, trichlorovinyl, etc.

Representative alkoxy groups which R, $R^1$ and $R^2$ may represent include methoxy, ethoxy, propoxy, isopropoxy, hexoxy, etc. Preferred alkoxy groups are alkoxy of 1 to 3 carbon atoms.

Representative cycloaliphatic groups which R, $R^1$ and $R^2$ can represent include cyclopropyl, cyclobutyl, cyclopentyl, cyclohexyl, cyclooctyl, cyclodecyl, cyclopropenyl, cyclobutenyl, cyclopentenyl, cycloheptenyl, cyclooctenyl, cyclodecenyl, chlorocyclopropyl, bromocyclohexyl, fluorocyclohexyl, chlorocyclooctenyl, etc.

Representative heterocyclic groups which R, $R^1$ and $R^2$ can represent include 2-pyridyl, 3-lutidyl, 2-pyrollyl, 2-thienyl, 2-furfuryl, 2-furylvinyl, 3-tetrahydrofurfuryl.

Representative aryl groups which R, $R^1$ and $R^2$ can represent include phenyl, 2-chlorophenyl, 3-chlorophenyl, 4-chlorophenyl, 2,3-dichlorophenyl, 2,4- dichlorophenyl, 2,5-dichlorophenyl, 2-fluorophenyl, 3-fluorophenyl, 4-fluorophenyl, 2-bromophenyl, 2,4-dibromophenyl, 4-bromophenyl, 2-chloro-4-bromophenyl, 4-methoxyphenyl, 2-ethoxyphenyl, 2-methylphenyl, 4-isopropylphenyl, 2,4-dimethylphenyl, 4-nitrophenyl, 2-nitro-4-methylphenyl, 3-sec.butylphenyl, naphthyl, 2-methyl-1-naphthyl, 2-trifluoromethylphenyl, 3-trifluoromethylphenyl, 3-chloro-4-bromophenyl.

Representative compounds of the present invention include:
4-methoxy-3,5-dioxo-1,2,4,6-thiatriazine,
2,4,6-trimethoxy-3,5-dioxo-1,2,4,6-thiatriazine,
2,4-dimethoxy-3,5-dioxo-6-ethyl-1,2,4,6-thiatriazine,
2,4,6-triethoxy-3,5-dioxo-1,2,4,6-thiatriazine,
2-propargyl-3,5-dioxo-6-ethoxy-1,2,4,6-thiatriazine,
2-cyclohexyl-3,5-dioxo-4-methoxy-1,2,4,6-thiatriazine,
3,5-dioxo-4,6-dibutoxy-1,2,4,6-thiatriazine,
2-methyl-3,5-dioxo-4-propoxy-6-allyl-1,2,4,6-thiatriazine,
2-fluoromethyl-3,5-dioxo-4-methoxy-1,2,4,6-thiatriazine,
2,4-dimethoxy-3,5-dioxo-6-(2-chloropropyl-1,2,4,6-thiatriazine,
2-(2-pyridyl)-3,5-dioxo-4-methoxy-1,2,4,6-thiatriazine,
2-methoxy-3,5-dioxo-4-(2-thienyl)-6-ethyl-1,2,4,6-thiatriazine,
3,5-dioxo-4-(2-furfuryl)-6-propoxy-1,2,4,6-ethyl-1,2,4,6-thiatriazine,
3,5-dioxo-4-(2-furfuryl)-6-methoxy-1,2,4,6-thiatriazine,
2,4,6-trimethoxy-3,5-dioxo-1,2,4,6-thiatriazine,
2-(2-fluorophenyl)-3,5-dioxo-4,6-dimethoxy-1,2,4,6-thiatriazine,
2-(2-pyrollyl)-3,5-dioxo-4-(2,4,6-trichlorophenyl)-6-methoxy-1,2,4,6-thiatriazine, etc.

Representative compounds of the present invention having one aryl group include the following:
2-(2-fluorophenyl)-3,5-dioxo-4-ethoxy-6-methyl-1,2,4,6-thiatriazine,
2-(2-chlorophenyl)-3,5-dioxo-4,6-diethoxy-1,2,4,6-thiatriazine,
2-(2-bromophenyl)-3,5-dioxo-4-methoxy-6-isopropyl-1,2,4,6-thiatriazine,
2-(2-chloro-4-bromophenyl)-3,5-dioxo-6-butoxy-1,2,4,6-thiatriazine,
2-(2-ethylphenyl)-3,5-dioxo-4-isopropoxy-6-allyl-1,2,4,6-thiatriazine,
2-(4-isopropoxyphenyl)-3,5-dioxo-4,6-dipropoxy-1,2,4,6-thriazine,
2-(2-methyl-4-bromophenyl)-3,5-dioxo-4-isopropoxy-6-methyl-1,2,4,6-thiatriazine,
2-(2-naphthyl)-3,5-dioxo-4,6-dimethoxy-1,2,4,6-thiatriazine,
2-(4-fluorophenyl)-3,5-dioxo-4-methoxy-1,2,4,6-thiatriazine,
2-(3-methoxy-4-bromophenyl)-3,5-dioxo-4-propargyl-6-methoxy-1,2,4,6-thiatriazine, etc.

Representative compounds of the present invention having two aryl groups are the following:
2,6-diphenyl-3,5-dioxo-4-propoxy-1,2,4,6-thiatriazine,
2,6-di-(2-fluorophenyl)-3,5-dioxo-4-methoxy-1,2,4,6-thiatriazine,
2,6-di-(2-fluorophenyl)-3,5-dioxo-4-ethoxy-1,2,4,6-thiatriazine,
2,6-di-(chloro-4-bromophenyl)-3,5-dioxo-4-isopropoxy-1,2,4,6-thiatriazine,
2,6-di-(3-methylphenyl)-3,5-dioxo-4-methoxy-1,2,4,6-thiatriazine,
2-(2-fluorophenyl)-3,5-dioxo-4-ethoxy-6-(3-methylphenyl)-1,2,4,6-thiatriazine,
2-(4-chlorophenyl)-3,5-dioxo-4-methoxy-6-(3-methylphenyl)-1,2,4,6-thiatriazine,
2-(2,4-dimethylphenyl)-3,5-dioxo-4-ethoxy-6-(2-fluorophenyl)-1,2,4,6-thiatriazine,
2,4-di-(2-fluorophenyl-3,5-dioxo-6-methoxy-1,2,4,6-thiatriazine, etc.

The compounds of this invention are prepared by the reaction of sulfur dichloride with an appropriate biuret-type compound, as follows:

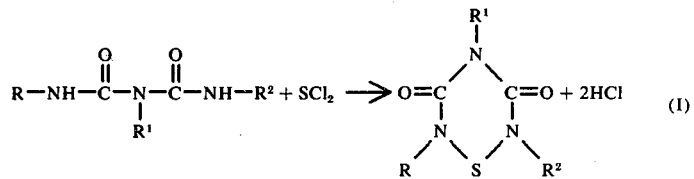

(I)

wherein R, $R^1$ and $R^2$ are as defined previously.

In this reaction (I) sulfur dichloride, preferably dissolved in a solvent, is added to the biuret, preferably dissolved in the same solvent. Sulfur dichloride is used in at least an equimolar amount or sometimes in a molar excess, up to about 20% based on the biuret. A solvent-soluble base is also present in the reaction to react with or tie up the hydrogen chloride by-product. For this purpose, the organic tertiary amines are preferred, e.g., pyridine, triethylamine, quinuclidine, N-methylpiperidine and the like. The solvents useful for this reaction are the inert halogenated hydrocarbons such as chloroform, carbon tetrachloride, dichloromethane, perchloroethylene, chlorobenzene, etc. Dichloromethane is preferred. The reaction is exothermic, and the temperature is usually maintained within the range of 0° to 40° C, preferably 10° to 20° C. Temperature control is accomplished by controlling the rate of addition of sulfur dichloride, by direct cooling or by reflux cooling. After all the reactants are added, the resulting mixture is stirred, preferably at about 20° C for ½ to 24 hours, preferably 1 to 2 hours. This reaction is usually carried out at atmospheric pressure, although higher or lower pressures may be used with appropriate equipment.

The product is isolated from the reaction mixture of reaction (I) by first washing with water to remove the amine hydrochloride salt. After drying, the organic solvent is removed by vaporization, usually by distillation or evaporation. The crude product obtained in this way may be used as such or it may be purified by distillation, crystallization or chromatography. The latter method is preferred.

For this reaction (I), freshly distilled sulfur dichloride is preferred. After standing for some time, sulfur dichloride equilibrates with formation of sulfur monochloride. Commerical sulfur dichloride is essentially an equilibrium mixture. When this mixture is used in the above reaction, many by-products are obtained and the yield of the desired 1,2,4,6-thiatriazine is very small.

The biuret-type compounds used as a feedstock in the above reaction (I) are obtained by the reaction of an appropriate isocyanate with an appropriate urea as follows:

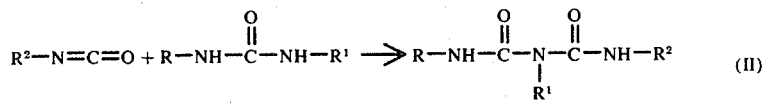

wherein R, R¹ and R² are as defined previously. This reaction (II) is well known, and is further described in U.S. Pat. No. 3,189,431.

Certain symmetrical compounds of this invention are made from symmetrical biurets, which in turn may be obtained by the reaction of 2 mols of an appropriate carbamoyl chloride and a primary amine, as follows:

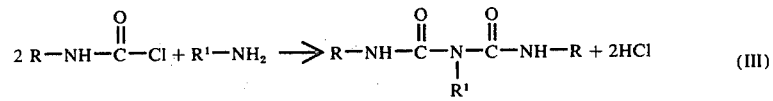

wherein R and R¹ are as defined previously. In this case R and R² are equivalent.

EXAMPLES

The following examples illustrate the method of preparation of the compounds of the subject invention. Unless otherwise indicated, percentages are by weight.

EXAMPLE 1 (a)

Preparation of 1,3-dimethyl-5-(2-fluorophenyl) biuret

To a solution of 8.8 g (0.1 mol) of 1,3-dimethyl urea dissolved in 30 ml of xylene there was added a solution of 13.7 g (0.1 mol) of 2-fluorophenylisocyanate dissolved in 30 ml of xylene. The resulting mixture was refluxed for 4 hours and then allowed to stand at ambient temperature for 16 hours. During this time the product crystallized and was removed by filtration. The product weighed 15.8 g. The NMR spectrum had a doublet at 2.86 ppm, a singlet at 3.25 ppm, and a multiplet structure at 7.2 ppm, characteristic of a biuret structure.

EXAMPLE 1 (b)

Preparation of 2-(2-fluorophenyl)-3,5-dioxo-4,6-dimethyl-1,2,4,6-thiatriazine

The product of Example 1 (a), 15.0 g (0.067 mol), was mixed with 100 ml of dichloromethane containing 10.6 g (0.134 mol) of pyridine. Then a solution of 6.9 g (0.067 mol) of freshly distilled sulfur dichloride in 35 ml of dichloromethane was added slowly. The resulting solution was stirred at ambient temperature for 2 hours. During this time a precipitate formed. The reaction mixture was washed with three 30-ml portions of water, dried and evaporated under vacuum to give a crude product. This material was mixed with ether, and the insoluble portion, about 2 g, was removed by filtration. The filtrate was then evaporated to give 13 g of an oil which was chromatographed on silica gel, using hexane, ether/hexane, and ether as the successive eluents. The ether portions contained 9.6 g of product which was oily in form. Analysis showed: %S, calc. 12.5, found 12.3. The NMR spectrum had a singlet at 3.2 ppm, a singlet at 3.25 ppm and a multiplet structure at 7.2 ppm, consistent with the assigned structure. The infrared spectrum had strong adsorption peaks at 730, 760–770, 825, 1100, 1360, 1440, 1500, 1675–1725 cm⁻¹.

EXAMPLE 2 (a)

Preparation of 1-methyl-3-methoxy-5-(2-fluorophenyl) biuret

To 35 g (0.27 mol) of 1-methyl-3-methoxy urea in 150 ml xylene was added dropwise a solution of 37 g (0.27 mol) 2-fluorophenylisocyanate in 100 ml of xylene. The reaction mixture was refluxed for 4 hours. The reaction mixture was filtered while warm to remove a small amount of triethylamine hydrochloride (impurity in the urea reactant). The filtrate was evaporated to give the biuret product as a solid (m.p. 144°–147° C after recrystallization from benzene). Elemental analysis for fluorine showed: calc. 7.88%, found 7.64%.

EXAMPLE 2 (b)

Preparation of 2-(2-fluorophenyl)-4-methoxy-6-methyl-3,5-dioxo-1,2,4,6-thiatriazine Sulfur dichloride, 7.95 g (0.077 mol) was added dropwise to a stirred solution of 15.5 g (0.064 mol) 1-methyl-3-methoxy-5-(2-fluorophenyl) biuret and 12.2 g (0.15 mol) pyridine in 100 ml dichloromethane. The reaction mixture was stirred at ambient temperature for 4 hours. The reaction mixture was filtered to remove the pyridine hydrochloride. The filtrate was washed successively with water, 5% aqueous sodium bicarbonate and water, dried over magnesium sulfate and stripped to give the crude thiatriazine product as an oil. The oil was taken up in ether and filtered through a silica gel column to give the product as an orange oil. Analysis for sulfur showed: calc. 11.8%, found 12.2%. The NMR spectrum showed a sharp 3-proton singlet at 3.5 ppm, a sharp 3-proton singlet at 4.1 ppm and a 4-proton multiplet centered at 7.4 ppm.

Other compounds were made by similar reactions. These are listed in Table I.

UTILITY

The thiatriazines of the present invention are, in general, herbicidal in both pre- and post-emergent applications. For pre-emergent control of undesirable vegetation, these thiatriazines will be applied in herbicidal quantities to the environment, e.g., soil infested with seeds and/or seedlings of such vegetation. Such application will inhibit the growth of or kill the seeds, germinating seeds and seedlings. For post-emergent applications the thiatriazines of the present invention will be applied directly to the foliage and other plant parts. Generally they are effective against weed grasses as well as broadleaved weeds. Some may be selective with respect to type of application and/or type of weed.

Pre- and post-emergnet herbicidal tests on representative thiatriazines of this invention were made using the following methods:

Pre-Emergent Test

An acetone solution of the test thiatriazine was prepared by mixing 750 mg. thiatriazine, 220 mg of a nonionic surfactant and 25 ml of acetone. This solution was added to approximately 125 ml of water containing 156 mg of surfactant.

Seeds of the test vegetation were planted in a pot of soil and the thiatriazine solution was sprayed uniformly onto the soil surface at a dose of 100 micrograms per $cm^2$. The pot was watered and placed in a greenhouse. The pot was watered intermittently and was observed for seedling emergence, health of emerging seedlings, etc., for a 3-week period. At the end of this period the herbicidal effectiveness of the thiatriazine was rated based on the physiological observations. A 0-to-100 scale was used, 0 representing no phytotoxicity, 100 representing complete kill.

Post-Emergent Test

The test thiatriazine was formulated in the same manner as described above for the pre-emergent test. The concentration to the thiatriazine in this formulation was 5000 ppm. This formulation was uniformly sprayed on 2 similar pots of 24-day-old plants (approximately 15 to 25 plants per pot) at a dose of 100 micrograms per $cm^2$. After the plants had dried, they were placed in a greenhouse and then watered intermittently at their bases as needed. The plants were observed periodically for phytotoxic effects and physiological and morphological responses to the treatment. After 3 weeks, the herbicidal effectiveness of the thiatriazine was rated based on these observations. A 0-to-100 scale was used, 0 representing no phytotoxicity, 100 representing complete kill.

The results of these tests appear in Table II. The concentration of compound No. 2 was 33 micrograms per $cm^2$ (instead of 100 micrograms per $cm^2$).

TABLE I

| No. | Compound | % Cl Calc. | % Cl Found | % S Calc. | % S Found | Melting Point, °C |
|---|---|---|---|---|---|---|
| 1 | 2-(2-fluorophenyl)-3,5-dioxo-4,6-dimethyl-1,2,4,6-thiatriazine | — | — | 12.5 | 12.3 | Oil |
| 2 | 2-(2-fluorophenyl)-3,5-dioxo-4-methoxy-6-methyl-1,2,4,6-thiatriazine | | | 11.8 | 12.2 | Oil |
| 3 | 2-(4-chlorophenyl)-3,5-dioxo-4,6-dimethyl-1,2,4,6-thiatriazine | 13.0 | 13.9 | 11.8 | 11.9 | Oil |
| 4 | 2-phenyl-3,5-dioxo-4,6-dimethyl-1,2,4,6-thiatriazine | — | — | 13.5 | 13.2 | Oil |
| 5 | 2-(3-methylphenyl)-3,5-dioxo-4,6-dimethyl-1,2,4,6-thiatriazine | — | — | 12.8 | 12.4 | Oil |
| 6 | 2-(3,4-dichlorophenyl)-3,5-dioxo-4,6-dimethyl-1,2,4,6-thiatriazine | 23.2 | 22.6 | 10.5 | 10.2 | 118–121 |
| 7 | 2-(4-methoxyphenyl)-3,5-dioxo-4,6-methyl-1,2,4,6-thiatriazine | — | — | 12.0 | 11.8 | 96.5–98 |
| 8 | 2-(2-fluorophenyl)-3,5-dioxo-6-methyl-1,2,4,6-thiatriazone | 7.1* | 7.2* | 11.9 | 12.1 | 210–211 |
| 9 | 2-(2-fluorophenyl)-3,5-dioxo-4-methyl-6-isopropyl-1,2,4,6-thiatriazone | — | — | 11.3 | 11.0 | semi-solid |

*fluorine analysis

TABLE II

| No. | Herbicidal Effectiveness — Pre/Post | | | | | |
|---|---|---|---|---|---|---|
| | O | W | C | M | P | L |
| 1 | 100/100 | 100/100 | 100/100 | 100/100 | 100/100 | 100/100 |
| 2 | 98/99 | 100/86 | 97/86 | 100/100 | 98/83 | 85/100 |
| 3 | 80/10 | 40/35 | 85/- | 80/100 | 95/95 | 85/100 |
| 4 | 100/100 | 100/100 | 100/100 | 95/100 | 90/100 | 95/100 |
| 5 | 100/60 | 100/100 | 100/50 | 100/100 | 100/60 | 100/95 |
| 6 | 20/- | 60/45 | 50/0 | 10/100 | -/35 | 10/70 |
| 7 | 35/10 | 50/45 | 20/- | 70/50 | 40/35 | 60/80 |
| 8 | 50/- | 15/- | 45/- | 70/20 | 80/40 | 90/25 |
| 9 | 20/45 | 40/90 | 45/75 | 100/95 | 55/95 | 80/100 |

O = Wild Oats (*Avena fatua*)
W = Watergrass (*Echinochloa crusgalli*)
C = Crabgrass (*digitaria sanguinalis*)
M = Mustard (*Brassica arvensis*)
P = Pigweed (*Amaranthus retroflexus*)
L = Lambsquarter (*Chenopodium album*)

The amount of thiatriazine administered will vary with the particular plant part or plant growth medium which is to be contacted, the general location of application, i.e., sheltered areas such as greenhouses as compared to exposed areas such as fields, as well as the desired type of control. For pre-emergent control of most plants, dosages in the range of about 0.5 to 20 lbs per acre will be used. Such administration will give a concentration of about 2 to 80 ppm thiatriazine distributed throughout 0.1 acre-foot. For post-emergent application, such as foliar spray application, compositions containing about 0.5 to 8 lbs thiatriazine per 100 gals spray will be used. Such application is equivalent to about 0.5 to 20 lbs thiatriazine per acre.

The herbicidal compositions of this invention comprise an herbicidal amount of one or more of the above-described thiatriazines intimately admixed with a biologically inert carrier. The carrier may be a liquid diluent such as water or acetone or a solid. The solid may be in the form of dust powder or granules. These compositions will also usually contain adjuvants such as a wetting or dispersing agent to facilitate their penetration into the plant growth medium or plant tissue and generally enhance their effectiveness. These compositions may also contain other pesticides, stabilizers, conditioners, fillers, and the like.

What is claimed is:

1. A compound of the formula

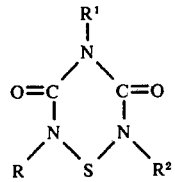

wherein R is alkyl of 1 to 4 carbon atoms; $R^1$ is alkoxy of 1 to 3 carbon atoms; and $R^2$ is phenyl substituted with 0 to 2 halogen atoms of atomic number 9 to 35, 0 to 1 alkyl group of 1 to 4 carbon atoms or 0 to 1 alkoxy group of 1 to 4 carbon atoms.

2. Compound of claim 1 wherein R is alkyl of 1 to 3 carbon atoms, $R^1$ is alkoxy of 1 to 3 carbon atoms, $R^2$ is phenyl substituted with 0 to 2 fluorine or chlorine atoms, 0 to 1 methyl group of 0 to 1 methoxy group.

3. Compound of claim 1 wherein R is methyl; $R^1$ is methoxy; and $R^2$ is 2-fluorophenyl.

* * * * *